(12) United States Patent
Leopoldo et al.

(10) Patent No.: US 9,260,400 B2
(45) Date of Patent: Feb. 16, 2016

(54) I-ARYLPIPERAZINIC LIGANDS OF 5-HT7 RECEPTOR AND USE THEREOF

(75) Inventors: Marcello Leopoldo, Bari (IT); Enza Lacivita, Bari (IT); Nicola Antonio Colabufo, Bari (IT); Paola De Giorgio, Bari (IT); Francesco Berardi, Bari (IT); Roberto Perrone, Bari (IT)

(73) Assignee: UNIVERSITA' DEGLI STUDI DI BARI "ALDO MORO", Bari (IT)

( * ) Notice: Subject to any disclaimer, the term of this patent is extended or adjusted under 35 U.S.C. 154(b) by 0 days.

(21) Appl. No.: 14/119,860

(22) PCT Filed: May 24, 2011

(86) PCT No.: PCT/EP2011/058419
§ 371 (c)(1),
(2), (4) Date: Nov. 23, 2013

(87) PCT Pub. No.: WO2012/159662
PCT Pub. Date: Nov. 29, 2012

(65) Prior Publication Data
US 2014/0086834 A1    Mar. 27, 2014

(51) Int. Cl.
| | |
|---|---|
| A61K 31/496 | (2006.01) |
| C07D 295/15 | (2006.01) |
| C07D 295/145 | (2006.01) |
| C07D 213/56 | (2006.01) |
| C07D 239/26 | (2006.01) |
| C07D 401/04 | (2006.01) |
| C07D 295/096 | (2006.01) |
| C07D 241/12 | (2006.01) |
| C07D 295/084 | (2006.01) |
| A61K 51/04 | (2006.01) |
| C07D 401/14 | (2006.01) |
| C07D 403/04 | (2006.01) |
| C07D 239/34 | (2006.01) |
| C07D 241/18 | (2006.01) |

(52) U.S. Cl.
CPC ........ *C07D 295/096* (2013.01); *A61K 51/0459* (2013.01); *C07D 239/26* (2013.01); *C07D 241/12* (2013.01); *C07D 295/084* (2013.01); *C07D 401/04* (2013.01); *C07D 401/14* (2013.01); *C07D 403/04* (2013.01)

(58) Field of Classification Search
None
See application file for complete search history.

(56) References Cited

U.S. PATENT DOCUMENTS

| | | | |
|---|---|---|---|
| 4,831,034 A * | 5/1989 | Barreau et al. | 514/252.16 |
| 6,818,644 B1 | 11/2004 | Lehmann-Lintz et al. | |
| 2011/0124657 A1 | 5/2011 | Pascual-Ramon | |

FOREIGN PATENT DOCUMENTS

| | | |
|---|---|---|
| DE | 199 45 594 | 3/2001 |
| EP | 0 211 457 | 2/1987 |
| WO | 2008/020306 | 2/2008 |
| WO | 2010/012811 | 2/2010 |

OTHER PUBLICATIONS

Walsh et al. J.Med.Chem. vol. 33, pp. 1823-1827 (1990).*
Leopoldo et al. "Structural Modifications of N-(1,2,3,4-tetrahydronapthalen-1-yl)-4-ary-I-piperazinehexanamides: Influence on lipophilicity and 5-HT7 receptor activity. Part III" *Journal of Medicinal Chemistry*, vol. 51, No. 18, pp. 5813-5822 (Sep. 2008).
Leopoldo et al. "Sertonin 5-HT7 receptor agents: Structure-activity relationships and potential therapeutic applications in central nervous system disorders" *Pharmacology & Therapeutics*, vol. 129, No. 2, pp. 120-148 (Oct. 2010).

(Continued)

*Primary Examiner* — Emily Bernhardt
(74) *Attorney, Agent, or Firm* — Nixon & Vanderhye PC

(57) ABSTRACT

The invention relates to a new class of compounds able to inhibit with high affinity and selectivity the 5-HT7 receptor and having the following formula IV:

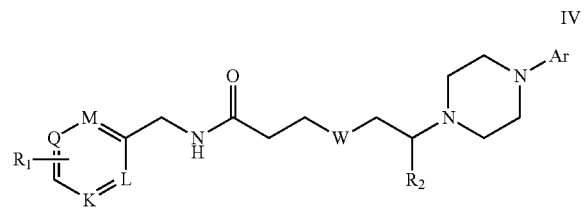

wherein W is O;
K, L, M and Q is CH or nitrogen;
$R_1$ is hydrogen;
$R_2$ is hydrogen; and
Ar is an aromatic ring with the following formula:

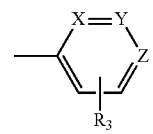

wherein X, Y and Z is CH; and $R_3$ is a five- or six-membered ring selected from the group consisting of:

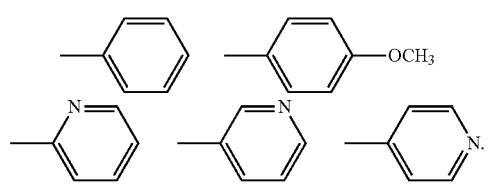

5 Claims, No Drawings

(56) References Cited

OTHER PUBLICATIONS

Int'l Search Report for PCT/EP2011/058419, six pages, mailed Jan. 20, 2012.

Written Opinion for PCT/EP2011/058419, ten pages, mailed Jan. 20, 2012.

* cited by examiner

I-ARYLPIPERAZINIC LIGANDS OF 5-HT7 RECEPTOR AND USE THEREOF

This application is the U.S. national phase of International Application No. PCT/EP2011/058419, filed 24 May 2011; the entire contents of which is hereby incorporated by reference.

TECHNICAL FIELD OF THE INVENTION

The invention relates to a new class of compounds able to inhibit with high affinity and selectivity the 5-HT7 receptor. The invention also relates to the utilization of such compounds as medicaments useful in the treatment and prevention of 5-HT7 receptor relating disorders of the central nervous system. The invention also relates to the isotopically labeled compounds for use in vivo diagnosis or imaging of a 5-HT7 condition.

BACKGROUND OF THE INVENTION

Serotonin (5-hydroxytryptamine, 5-HT) elicits a multitude of physiological effects through the interaction with at least fourteen receptors that have been grouped on the basis of molecular, pharmacological, and functional criteria into seven discrete families (5-HT1-7) [1]. The 5-HT7 receptor was identified starting from 1993 by the application of targeted molecular biology techniques. It has been described in various species and remains the last 5-HT receptor to be discovered. The 5-HT7 receptor has been localized in discrete areas of the brain and in the periphery. Within the central nervous system this receptor has been detected in high levels in the thalamus, hippocampus, and hypothalamus (especially within the suprachiasmatic nucleus, SCN) [2]. Much information is available on the pathophysiological role of 5-HT7 receptor in the central nervous system. The availability of the selective 5-HT7 antagonist SB-269970 and of 5-HT7-knockout mice has allowed relevant insight into the role of 5-HT7 receptors in depression. As an example, pharmacological blockade of 5-HT7 receptor or inactivation of the receptor gene leads to an antidepressant-like behavioral profile in rodent models of depression (forced swim test and tail suspension test) [3]. Recently, it has been suggested that the atypical antipsychotic drug amisulpride exerts its antidepressant action through blockade of 5-HT7 receptors [4]. It should also be noted that the atypical antipsychotic aripiprazole has high affinity for the 5-HT7 receptor [5,6] and it is successfully used to augment the effect of traditional antidepressants [7]. These findings further support the potential of 5-HT7 receptor antagonists to yield a novel class of antidepressant drugs. The recent availability of selective agonists such as AS-19 and E-55888 is opening up new scenarios on the therapeutic actions of 5-HT7 receptor activation. It has been demonstrated that behavioral antinoception can be achieved by systemic administration of AS-19 or E-55888 [8]. Also, AS-19 has served to demonstrate the involvement of 5-HT7 receptor in memory formation [9]. In addition, it has been found that the stimulation of cultured striatal neurons with the mixed 5-HT1A/7 agonist, 8-OH-DPAT, induced a marked neurite outgrowth. This effect was specifically triggered by 5-HT7 receptor activation, because it was blocked by application of SB-269970 [10]. These data supported the crucial role of this receptor in the modulation of neuronal morphology, as also observed in mouse hippocampal neurons following 5-HT7 receptor activation [11].

The international application WO2008146064A1 disclosed some benzofuran compounds that bind 5-hydroxy triptamine-7 receptor for use in the treatment or prevention of disorders of central nervous system and/or cardiovascular disorders.

The compounds reported in the state of the art with high affinity for the 5-HT7 receptor suffer from the lack of selectivity over a range of 5-HT receptors. Also, the most potent 5-HT7 ligands proposed to date are not sufficiently metabolically stable. This precludes the use of such compounds as in vivo tools for studying the function of 5-HT7 receptor and as drugs. Moreover, to date no positron emission tomography tracer is available to visualize 5-HT7 receptor in either central nervous system or periphery.

SUMMARY OF THE INVENTION

The present invention relates to new compounds that present high affinity and selectivity for 5-HT7 receptors as well as good pharmacokinetic properties. Several 5-HT7 ligands reported in literature have not been characterized regarding their metabolic liability or, when these data are available, they demonstrated a very short half-life time that limits their in vivo use. As example, plasma and brain concentration of LP-44 [12] became undetectable after 20 minutes following i.p injection. The compounds of the present invention exhibit chemical features (i.e.: electron-withdrawing groups) that make them less metabolically liable. Moreover, the compounds of the present invention possess optimal lipophilicity (2<logP>3.5) for both in vivo use and for the development of a brain PET tracer. It is well-known that high lipophilicity reflects in high metabolic liability when administered in vivo and in low image resolution in PET imaging.

Finally, the compounds described in the present invention present structural features that allow easy radiolabelling with positron emitter radioisotopes.

Hence, object of the present invention is a family of compounds having the general formula as indicated in claim 1.

A second object of the invention is a family of compounds having the general formula as indicated in claim 2.

A third object of the invention are compounds selected from the above-indicated families isotopically radiolabeled.

A fourth object of the invention are compounds selected from the above-indicated families for use as medicaments, advantageously for use in the treatment of any condition susceptible of being improved or prevented by selective occupation of the 5-HT7 receptor.

A fifth object of the invention are compounds isotopically radiolabeled selected from the above-indicated families for use in vivo diagnosis or imaging of a 5-HT7 condition.

A further object of the invention are a pharmaceutical composition comprising the compounds of the invention and a pharmacologically acceptable excipient.

Other objects will be made evident in the light of the following detailed description.

The results reported in the experimental part demonstrate that compounds of the invention are able to bind with high affinity and selectivity the 5-HT7 receptor.

DETAILED DESCRIPTION OF THE INVENTION

Compounds of the Invention

The invention relates to a family of novel compounds having the following general formula I thereof:

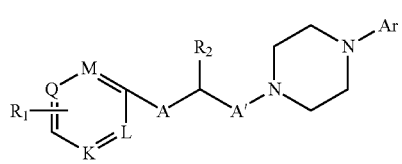

wherein

A¹ is a direct bond between CH[R₂] and the piperazine group or $C_{1-3}$ Alkyl group;

A is a direct bond between CH[R₂] and the heterocyclic ring or —OCH₂— or —CH₂—NH—CO—CH₂—CH₂—O—CH₂— or —CH₂—NH—CO—CH₂—CH₂—CH₂—CH₂—;

K, L, M, and Q is CH or nitrogen;

R₁ is selected from the group consisting of hydrogen, $(CH_2)_nF$, $(CH_2)_nOCH_3$, $O(CH_2)_nF$ and n is between 1 and 3;

R₂ is a hydrogen or —OH or F;

Ar is an aromatic ring with the following formula:

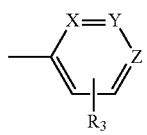

wherein X, Y and Z is CH or nitrogen and R₃ is a five or six membered ring selected in the following group:

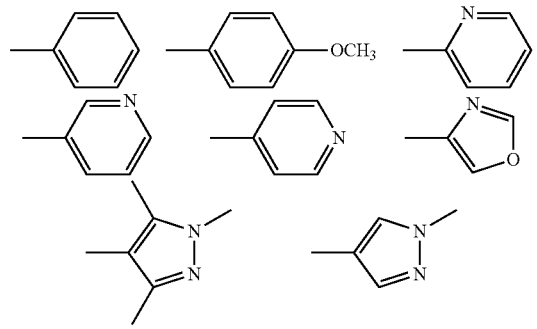

The compounds of formula I may contain one or more chiral centers and can exist in different stereoisomeric forms, such as racemic mixtures, single enantiomers, enantiomeric enriched mixtures, individual diastereoisomers and diastereomeric mixtures. All stereoisomeric forms of the intermediates and compounds of the present invention as well as mixtures thereof, which possess properties useful for the application discussed herein or are intermediates useful in the preparation of compounds having such properties, form part of the present invention.

Racemic mixture can be separated into each enantiomer using standard conditions, such as resolution or chiral chromatography. Diastereoisomeric mixtures may be separated into their individual diastereoisomers on the basis of their physical chemical differences by methods well known to those skilled in the art, such as by chiral chromatography using an optically active stationary phase and/or fractioned crystallization from suitable solvent. Enantiomers and diastereoisomers may be separated by use of a chiral HPLC column and by converting the enantiomeric mixture into a diastereomeric mixture by reaction with an appropriate optically active compound separating the diastereoisomers and converting the individual diastereoisomers to the corresponding pure enantiomers. Alternatively, any stereoisomer of a compound of general formula I may be obtained by stereospecific synthesis using optically pure starting materials or reagents of known absolute configuration.

A specific subgroup of the general formulas indicated above comprises compounds having the following formula II:

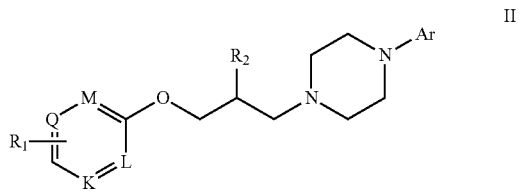

A second subgroup of the general formula I indicated above comprises compounds having the following formula III:

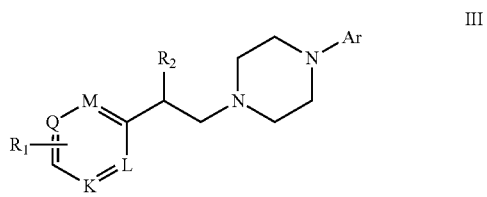

A third subgroup of the general formula I indicated above comprises compounds having the following formula IV:

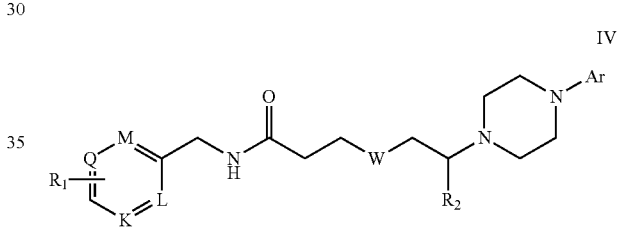

wherein W is CH₂ or O.

Specific examples of compounds of the invention are:
1-(4-Methoxyphenoxy)-3-[4-(2-biphenyl)piperazin-1-yl]propan-2-ol,
1-[4-[2-(4-Methoxyphenyl)phenyl]piperazin-1-yl]-3-phenoxy-propan-2-ol,
1-(4-Methoxyphenoxy)-3-[4-[3-(2-pyridyl)-2-pyridyl]piperazin-1-yl]propan-2-ol,
1-(4-Methoxyphenoxy)-3-[4-[3-(3-pyridyl)-2-pyridyl]piperazin-1-yl]propan-2-ol,
1-(4-Methoxyphenoxy)-3-[4-[3-(4-pyridyl)-2-pyridyl]piperazin-1-yl]propan-2-ol,
1-[4-(2-Fluoroethoxy)phenoxy]-3-[4-[3-(2-pyridyl)-2-pyridyl]piperazin-1-yl]propan-2-ol,
1-[4-(2-Fluoroethoxy)phenoxy]-3-[4-[3-(3-pyridyl)-2-pyridyl]piperazin-1-yl]propan-2-ol,
1-[4-(2-Fluoroethoxy)phenoxy]-3-[4-[3-(4-pyridyl)-2-pyridyl]piperazin-1-yl]propan-2-ol,
1-[4-[2-(4-Methoxyphenyl)phenyl]piperazin-1-yl]-3-pyrimidin-2-yloxy-propan-2-ol,
1-[4-[2-(4-Methoxyphenyl)phenyl]piperazin-1-yl]-3-pyrazin-2-yloxy-propan-2-ol,
1-[4-[2-(4-Methoxyphenyl)phenyl]piperazin-1-yl]-3-pyrimidin-4-yloxy-propan-2-ol,
1-[2-Fluoro-2-(3-methoxyphenyl)ethyl]4-[3-(2-pyridyl)-2-pyridyl)piperazine,
1-[2-Fluoro-2-(3-methoxyphenyl)ethyl]4-[3-(3-pyridyl)-2-pyridyl)piperazine, 1-[2-Fluoro-2-(3-methoxyphenyl)ethyl]4-[3-(4-pyridyl)-2-pyridyl)piperazine,
1-[2-(3-Methoxyphenoxy)ethyl]4-[3-(2-pyridyl)-2-pyridyl]piperazine,
1-[2-(3-Methoxyphenoxy)ethyl]4-[3-(3-pyridyl)-2-pyridyl]piperazine,
1-[2-(3-Methoxyphenoxy)ethyl]4-[3-(4-pyridyl)-2-pyridyl]piperazine,
1-[2-[4-(2-Fluoroethoxy)phenoxy]ethyl]4-[3-(2-pyridyl)-2-pyridyl]piperazine,
1-[2-[4-(2-Fluoroethoxy)phenoxy]ethyl]4-[3-(3-pyridyl)-2-pyridyl]piperazine,
1-[2-[4-(2-Fluoroethoxy)phenoxy]ethyl]4-[3-(4-pyridyl)-2-pyridyl]piperazine,
4-[2-(4-Methoxyphenyl)phenyl]-N-(2-pyridinylmethyl)-1-piperazinehexanamide,
4-[2-(4-Methoxyphenyl)phenyl]-N-(3-pyridinylmethyl)-1-piperazinehexanamide,
4-[2-(4-Methoxyphenyl)phenyl]-N-(4-pyridinylmethyl)-1-piperazinehexanamide,
N-[(4-Methoxyphenyl)methyl]-6-[4-[3-(2-pyridyl)-2-pyridyl]piperazin-1-yl]hexanamide,
N-[(4-Methoxyphenyl)methyl]-6-[4-[3-(3-pyridyl)-2-pyridyl]piperazin-1-yl]hexanamide,
N-[(4-Methoxyphenyl)methyl]-6-[4-[3-(4-pyridyl)-2-pyridyl]piperazin-1-yl]hexanamide,
3-[2-[4-[2-(4-Methoxyphenyl)phenyl]piperazin-1-yl]ethoxy]-N-(2-pyridylmethyl)propanamide,
3-[2-[4-[2-(4-Methoxyphenyl)phenyl]piperazin-1-yl]ethoxy]-N-(3-pyridylmethyl)propanamide,
3-[2-[4-[2-(4-Methoxyphenyl)phenyl]piperazin-1-yl]ethoxy]-N-(4-pyridylmethyl)propanamide,
N-[(4-Methoxyphenyl)methyl]-3-[2-[4-[3-(2-pyridyl)-2-pyridyl]piperazin-1-yl]ethoxy]propanamide,
N-[(4-Methoxyphenyl)methyl]-3-[2-[4-[3-(3-pyridyl)-2-pyridyl]piperazin-1-yl]ethoxy]propanamide,
N-[(4-Methoxyphenyl)methyl]-3-[2-[4-[3-(4-pyridyl)-2-pyridyl]piperazin-1-yl]ethoxy]propanamide.

Compounds of the Invention Isotopically Labeled

The present invention also encompasses isotopically radio-labeled compounds which are identical to the compounds of formula I, II, III and IV or intermediates thereof but for the fact that one or more atoms are replaced by an atom having atomic mass or mass number different from the atomic mass or mass number usually found in nature. Example of isotopes that can be incorporated into the intermediates or compounds of the invention include isotopes of hydrogen, carbon, nitrogen, oxygen and fluorine, such as $^{3}H$, $^{11}C$, $^{14}C$, $^{13}N$, $^{15}O$, $^{18}F$, respectively.

Method For Preparing the Compounds of the Invention

The compounds of formula II, III and IV of the present invention can be prepared according the procedures of the following Schemes. Suitable reaction conditions for the steps of these schemes are well known in the art and appropriate substitutions of solvents and co-reagents are within the skill of the art. The synthetic intermediates may be isolated and/or purified by various well known techniques.

Reaction Scheme 1 illustrates the methods employed in the synthesis of the compounds of formula I. All substituent are as defined above unless indicated otherwise.

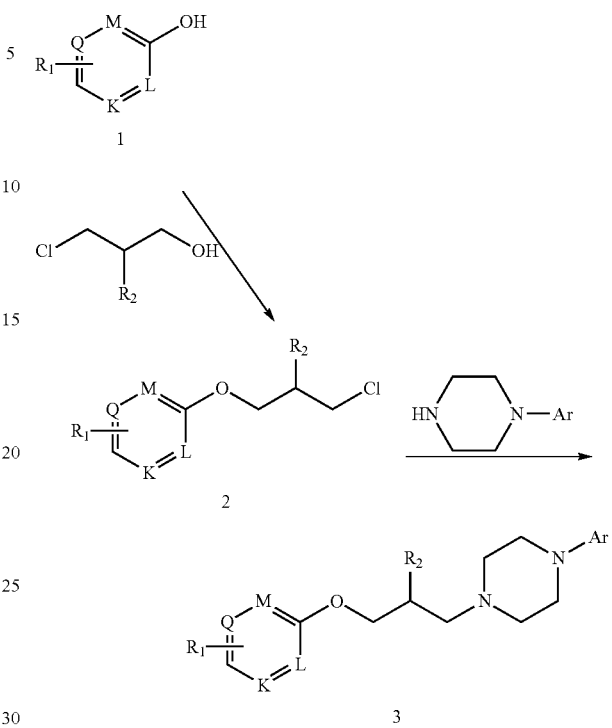

Scheme 1

In Scheme 1, an appropriately substituted phenol 1 reacted with the appropriate epichlorohydrin compound to give an oxirane 2. The reaction with the appropriate 1-arylpiperazine afforded compound 3.

Reaction Scheme 2 illustrates the methods employed in the synthesis of the compounds of formula III. All substituent are as defined a bove unless indicated otherwise.

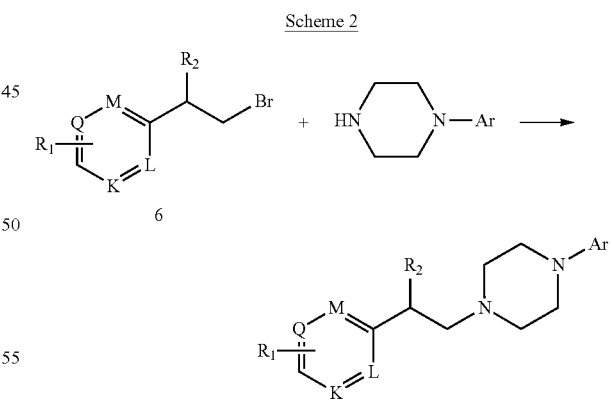

Scheme 2

In Scheme 2, an appropriately substituted 2-bromoethanone 6 reacted with the appropriate 1-arylpiperazine to obtain compound 7.

Reaction Scheme 3 illustrates the methods employed in the synthesis of the compounds of formula IV. All substituents are as defined above unless indicated otherwise.

Scheme 3

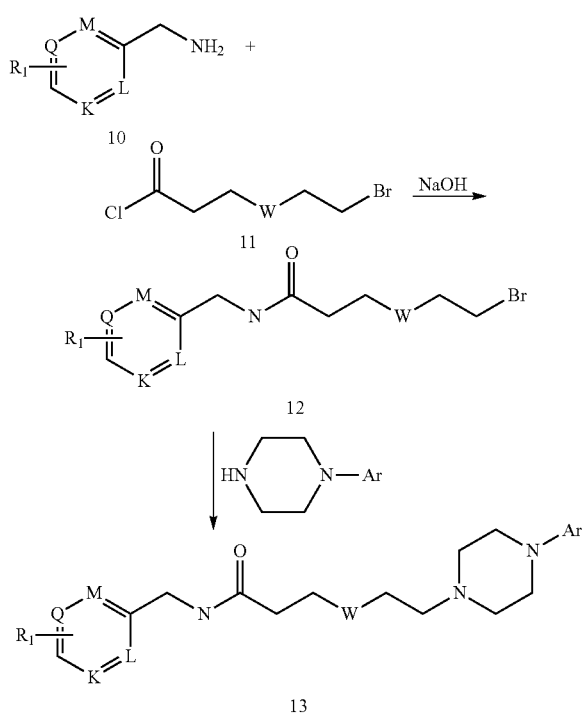

In Scheme 3, an appropriately substituted amine 10 reacted with the appropriate bromoalkanoylchloride 11 to give the amide 12. The reaction with the appropriate 1-arylpiperazine afforded compound 13.

General Procedure For Radiosynthesis

The incorporation of radioactive fluorine atom into the compounds of formula (I) may be performed using techniques known in the art, for example by reaction of a suitable precursor, bearing a leaving groups, such as mesylate, triflate, nitro, tosylate, bromine, with a nucleophilic radioactive fluorinating reagent, such as K[$^{18}$F]/Kriptofix®222 or tetralkyl ammonium salts incorporating radioactive fluoride. The reaction is carried out in an inert solvent such as, dimethylformamide, stirring the reaction mixture at a suitable temperature, typically at 100° C., using conventionally heating or under microwave irradiation, for the required time to achieve completion of the reaction. The incorporation of radioactive 11-Carbon atom into the compounds of formula (I) may be performed, for example by reaction of a suitable precursors bearing a phenolic hydroxyl group with radioactive methylating reagent, such as [$^{11}$C]CH3I, [$^{11}$C]CH3OTf. The reaction is performed in an inert solvent such as dimethylformamide, in the presence of a strong base, such as NaOH, stirring the reaction mixture at a suitable temperature until complete achievement of the reaction.

Therapeutic Applications

A further object of the present invention is a compound selected from the above-indicated families for use as medicament.

The compounds of the invention able to inhibit with high affinity and selectivity the 5-HT7 receptor activity find therapeutic applications in the treatment of any condition susceptible of being improved or prevented by selective occupation of the 5-HT7 receptor.

Disorders of the central nervous system linked to the 5-HT7 receptor activity comprise migraine, anxiety, persistent pain, inflammatory pain, neuropathic pain, depression, anxiety.

Compounds of the Invention Isotopically Labeled for use in vivo Diagnosis or Imaging.

Isotopically labeled compounds of the present invention are useful in vivo diagnosis or imaging of a 5-HT7 condition. For example compounds labeled with positron emitting isotopes such as $^{11}$C, $^{13}$N, $^{15}$), $^{18}$F are useful for Positron Emission Tomography (PET) analysis.

Radiotracers of the present invention are useful for assessing 5-HT7 receptors using PET, particularly in patient populations and preferably in subjects having or being diagnosed disorders as described herein. Further, radiotracers of the present invention are useful in drug development and drug discovery, for example, in neuroscience to assess interaction of drugs with 5-HT7 receptors or substrate occupancy.

Pharmaceutical Compositions

A further object of the invention is a pharmaceutical composition comprising the compounds selected from the above-indicated families and a pharmacologically acceptable excipient and/or carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, acetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin. Thus, based on the above, a variety of pharmaceutically acceptable doses are provided.

Also, it is noted that the term "pharmaceutically acceptable salt(s)" refers to salts derived from treating a compound of formula 1 with an organic or inorganic acid such as, for example, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, or benzoic.

The pharmaceutical compositions of the invention are useful in the treatment and prevention of 5-HT7 receptor relating disorders of the central nervous system, in particular for use in the treatment of migraine, anxiety, persistent pain, inflammatory pain, neuropathic pain, depression, anxiety.

Imaging Composition

A further object of the invention is a diagnostic imaging composition comprising as imaging agent the compounds selected from the above-indicated families isotopically labeled and a carrier. In accordance with the invention, the radiolabeled compounds according to Formula I, II, III or IV may be administered in a single unit injectable dose. Any of the common carriers known to those with skill in the art, such as sterile saline solution or plasma, can be utilized after radiolabelling for preparing the injectable solution to diagnostically imaging in accordance with the invention. Such techniques include the step of bringing into association the active ingredient and the pharmaceutical carrier(s) or diluent(s). In general the formulations are prepared by uniformly and intimately bringing into association the active ingredient with the liquid carrier.

The unit dose to be administered for a diagnostic agent has a sufficient radioactivity when they are, for example, 150 MBq. Higher or lower radioactivity may be used according to the circumstances. For diagnostic purposes after intravenous administration, imaging of the organ in vivo can take place in a matter of a few minutes. However, imaging takes place, if desired, in hours or even longer, after injecting into patients. In most instances, a sufficient amount of the administered dose will accumulate in the area to be imaged within about 1 hour to permit the taking of diagnostic images. Any conventional method of imaging for diagnostic purposes can be utilized in accordance with this invention as positron emission tomography (PET) or Single photon emission computed tomography (SPECT).

The diagnostic imaging compositions of the invention are useful for use in vivo diagnosis or imaging of a 5-HT7 condition.

Method For Treatment

It is a further object of the invention a method for treating a disorder of the central nervous system that can be treated by modulating serotonergic neurotransmission in a mammal, comprising administering to a mammal requiring such treatment, preferably a human, an effective amount of a compound of the families described above. In particular for treating the disorder of the central nervous system selected from migraine, anxiety, persistent pain, inflammatory pain, neuropathic pain, depression, anxiety.

In the method of treatment the effective amount administered and frequency of administration of the compounds of the present invention will depend on the particular condition to be treated, the severity of the condition to be treated, age, weight and the overall physical condition of the particular patient as well as on other medicaments the patient is taking, as it is well known to the experts in the field.

The effective amount of the compounds of the invention to be administered daily or per dosage, is within a range of from 0.1 ng to 100 mg per kg body weight, preferably within a range of from 1 ng to 10 mg per kg body weight.

Method for in vivo Diagnosis

It is a further object of the invention an in vivo method for diagnosis of a 5-HT7 condition, comprising:

administering to a mammal, preferably a human, an effective amount of a isotopically labeled compound of the families described above;

imaging the in vivo 5-HT7 receptor.

The imaging technique may be for example Positron emission tomography (PET) or Single positron emission computerized tomography (SPECT).

In the method of in vivo diagnosis the effective amount administered of the isotopically labelled compounds of the present invention will depend on the particular condition to be diagnosed, the age, weight and the overall physical condition of the particular patient as it is well known to the experts in the field.

The diagnostically effective amount of the labeled or unlabeled compounds of the present invention to be administered before conducting the in vivo diagnosis is within a range from 0.1 ng to 100 mg per kg body weight, preferably within a range of from 1 ng to 10 mg per kg body weight.

EXAMPLES AND BIOLOGICAL EXPERIMENTATION

The invention is detailed hereinafter via the following examples of preparation and through the following biological testing.

By the methods described above the following intermediates and final compounds have been obtained.

EXAMPLES

Specific Reaction Schemes

Reaction Scheme 1 illustrates the methods employed in the synthesis of some compounds of the general formula II. All substituents are as defined above unless indicated otherwise.

Scheme 1

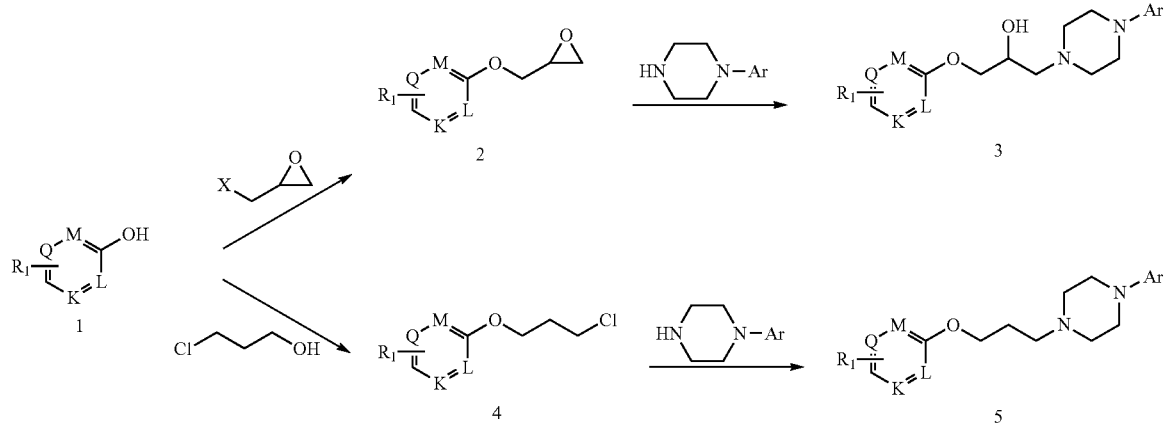

In Scheme 1, an appropriately substituted phenol 1 reacted with epichlorohydrin or glycidol to give the oxirane 2. The reaction with the appropriate 1-arylpiperazine afforded compound 3. Alternatively, an appropriately substituted phenol 1 reacted with 3-chloro-1-propanol under Mitsunobu conditions to give the alkylating agent 4. The reaction with the appropriate 1-arylpiperazine gave compound 5.

Reaction Scheme 2 illustrates the methods employed in the synthesis of the some compounds of the general formula III. All substituents are as defined above unless indicated otherwise.

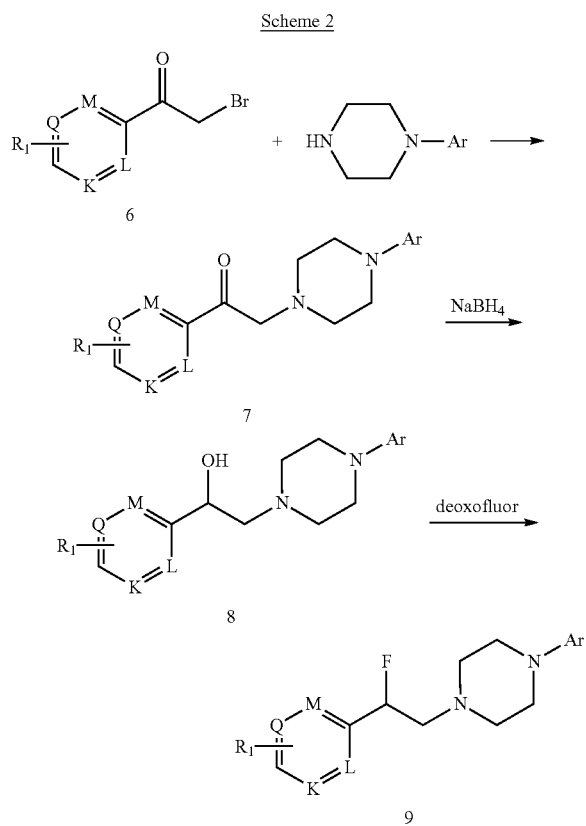

Scheme 2

In Scheme 2, an appropriately substituted 2-bromoethanone 6 reacted with the appropriate 1-arylpiperazine to obtain compound 1. Reduction of ketone 7 afforded alcohol 8 which reacted with deoxofluor to give compound 9.

Example 1

1-(4-Methoxyphenoxy)-3-[4-(2-biphenyl)piperazin-1-yl] propan-2-ol 1A) 2-[(4-methoxyphenoxy)methyl]oxirane A solution of NaOH (0.35 g) in 10 mL of water was added to a mixture of 4-methoxyphenol (1.10 g, 8.5 mmol) and epichlorohydrin (0.80 mL, 10.2 mmol). The mixture was heated at 100° C. for 3 h. After cooling, the mixture is taken up with AcOEt (50 mL). The organic phase was separated, washed with brine, dried over $Na_2SO_4$ and evaporated under reduced pressure. The crude residue was chromatographed (Petroleum ether/AcOEt, 4:1, as eluent) to afford pure compound in 48% yield. $^1$H NMR ($CDCl_3$): δ 2.73-2.75 (m, 1H), 2.89 (app t, 1H), 3.31-3.36 (m, 1H), 3.76 (s, 3H), 3.88-3.93 (m, 1H), 4.14-4.20 (m, 1H), 6.81-6.88 (m, 4H).

1B) 1-(4-Methoxyphenoxy)-3-[4-(2-biphenyl)piperazin-1-yl]propan-2-ol

A Mixture of 2-[(4-methoxyphenoxy) methyl]oxirane (2.2 mmol) and 1-[3-(2-pyridyl)-2-pyridyl]piperazine (2.2 mmol) in EtOH (20 mL) was heated under reflux for 3 h. Then, the solvent was evaporated under reduced pressure and the crude residue was chromatographed ($CHCl_3$/MeOH 19.1) to yield pure compound. $^1$HE NMR ($CDCl_3$): δ 2.35-2.38 (m, 3H, 1H $D_2O$ exchanged), 2.49-2.60 (m, 4H), 2.82-2.92 (m, 4H), 3.76 (s, 3H), 3.91 (d, 2H, J=5.0 Hz), 4.01-4.07 (m, 1H), 6.80-6.87 (m, 4H), 7.03-7.11 (m, 2H), 7.24-7.32 (m, 3H), 7.50 (t, 2H, J=7.5 Hz), 7.63 (d, 2H, J=1.1 Hz). $ESI^+$/MS m/z 419.1 ($MH^+$). $ESI^+$/MS/MS m/z 255.1 (82), 236.1 (95), 194.1 (100).

Example 2

1-[4-[2-(4-Methoxyphenyl)phenyl]piperazin-1-yl]-3-phenoxy-propan-2-ol

Title compound was prepared starting from Example 1A and 1-[2-(4-methoxyphenyl)phenyl]piperazine following the procedure outlined for Example 1B. $^1$H NMR ($CDCl_3$): δ 2.35-2.38 (m, 3H, 1H $D_2$O exchanged), 2.49-2.60 (m, 4H), 2.82-2.92 (m, 4H), 3.80 (s, 3H), 3.91 (d, 2H, J=5.0 Hz), 4.01-4.07 (m, 1H), 6.33 (dd, 1H, J=1.9, 7.4 Hz), 6.60-6.65 (m, 3H), 6.72-6.75 (m, 2H), 6.77-6.81 (m, 4H), 7.09-7.13 (m, 1H), 7.16-7.22 (m, 2H). $ESI^+$/MS m/z 419.1 ($MH^+$). $ESI^+$/MS/MS m/z 255.1 (82), 236.1 (95), 194.1 (100).

Example 3

1-(4-Methoxyphenoxy)-3-[4-[3-(2-pyridyl)-2-pyridyl]piperazin-1-yl]propan-2-ol

The title compound was prepared starting from Example 1A and 1-[3-(2-pyridyl)-2-pyridyl]piperazine following the procedure outlined for Example 1B. $^1$H NMR ($CDCl_3$): δ 2.34-2.42 (m, 3H, 1H $D_2$O exchanged), 2.49-2.70 (m, 4H), 3.14 (br s, 4H), 3.76 (s, 3H), 3.92 (d, 2H, J=4.7 Hz), 4.02-4.07 (m, 1H), 6.80-6.87 (m, 4H), 6.98 (dd, 1H, J=7.4 Hz), 7.20-7.25 (m, 1H), 7.71 (dt, 1H, J=1.6, 7.4 Hz), 7.83 (dd, 1H, J=1.9, 7.4 Hz), 7.88-7.91 (m, 1H), 8.27 (dd, 1H, J=1.9, 4.9 Hz), 8.69-8.72 (m, 1H). GC-MS m/z 421 ($M^+$1, 1), 420 ($M^+$, 3), 254 (100), 198 (35), 184 (50), 172 (25).

Example 4

1-(4-Methoxyphenoxy)-3-[4-[3-(3-pyridyl)-2-pyridyl]piperazin-1-yl]propan-2-ol

The title compound was prepared from Example 1A and 1-[3-(3-pyridyl)-2-pyridyl]piperazine following the procedure outlined for Example 1B. $^1$H NMR ($CDCl_3$): δ 2.33-2.37 (m, 3H, 1H $D_2$O exchanged), 2.48-2.59 (m, 4H), 2.83-2.95 (m, 4H), 3.76 (s, 3H), 3.93 (d, 2H, J=5.0 Hz), 4.01-4.07 (m, 1H), 6.79-6.89 (m, 4H), 6.96 (dd, 1H, J=7.4 Hz), 7.33-7.37 (m, 1H), 7.45-7.48 (m, 1H), 7.97 (dt, 1H, J=1.9, 7.7 Hz), 8.28 (dd, 1H, J=1.9, 4.9 Hz), 8.56 (dd, 1H, J=1.7, 4.9 Hz), 8.82 (d, 1H, J=1.7 Hz). GC-MS m/z 421 ($M^+$1, 3), 420 ($M^+$, 8), 254 (100), 198 (29), 184 (63), 172 (45).

Example 5

1-(4-Methoxyphenoxy)-3-[4-[3-(4-pyridyl)-2-pyridyl]piperazin-1-yl]propan-2-ol The title compound was prepared from Example 1A and 1-[3-(4-pyridyl)-2-pyridyl]piperazine following the procedure outlined for Example 1B. $^1$H NMR (CDCl$_3$): δ 2.34-2.42 (m, 3H, 1H D$_2$0 exchanged), 2.49-2.70 (m, 4H), 3.14 (br s, 4H), 3.76 (s, 3H), 3.92 (d, 2H, J=4.7 Hz), 4.02-4.07 (m, 1H), 6.80-6.87 (m, 4H), 6.96 (dd, 1H, J=7.4 Hz), 7.48 (dd, 1H, J=1.9, 7.4 Hz), 7.58 (d, 2H, J=4.7 Hz), 8.29 (dd, 1H, J=1.9, 4.9 Hz), 8.66 (d, 2H, J=4.9 Hz). GC-MS m/z 421 (M$^+$1, 1), 420 (M$^+$, 3), 253 (85), 198 (70), 184 (100), 172 (45).

Example 6

1-[4-(2-Fluoroethoxy)phenoxy]-3-[4-[3-(2-pyridyl)-2-pyridyl]piperazin-1-yl]propan-2-ol

6A) 2-[[4-(2-fluoroethoxy)phenoxy]methyl]oxirane

A solution of NaOH (0.35 g) in 10 mL of water was added to a mixture of 4-(2-fluoroethoxy) phenol (1.10 g, 7.1 mmol) and epichlorohydrin (0.80 mL, 10.2 mmol). The mixture was heated at 100° C. for 3 h. After cooling, the mixture is taken up with AcOEt (50 mL). The organic phase was separated, washed with brine, dried over Na$_2$SO$_4$ and evaporated under reduced pressure. The crude residue was chromatographed (Petroleum ether/AcOEt, 4:1, as eluent) to afford pure compound in 48% yield. $^1$H NMR (CDCl$_3$): δ 2.60-2.70 (m, 2H), 3.16 (m, 1H), 3.89-4.04 (m, 2H), 4.17-4.28 (m, 1H), 4.50-4.65 (m, 1H), 6.54 -6.60 (m, 2H), 6.84-6.87 (m, 2H).

6 B) 1-[4-(2-Fluoroethoxy)phenoxy]-3-[4-[3-(2-pyridyl)-2-pyridyl]piperazin-1-yl]propan-2-ol The title compound was prepared from Example 6A and 1-[3-(2-pyridyl)-2-pyridyl]piperazine following the procedure outlined for Example 1B. $^1$H NMR (CDCl$_3$): δ 2.34-2.42 (m, 3H, 1H D$_2$O exchanged), 2.49-2.70 (m, 4H), 3.14 (br s, 4H), 3.92 (d, 2H, J=4.7 Hz), 4.02-4.07 (m, 1H), 4.17-4.28 (m, 1H), 4.50-4.65 (m, 1H), 6.54 -6.60 (m, 2H), 6.84-6.87 (m, 2H), 6.98 (dd, 1H, J=7.4 Hz), 7.20-7.25 (m, 1H), 7.71 (dt, 1H, J=1.6, 7.4 Hz), 7.83 (dd, 1H, J=1.9, 7.4 Hz), 7.88-7.91 (m, 1H), 8.27 (dd, 1H, J=1.9, 4.9 Hz), 8.69-8.72 (m, 1H). GC-MS m/z 453 (M$^+$1, 1), 452 (M$^+$, 3), 432 (25), 254 (100), 198 (35), 172 (25).

Example 7

1-[4-(2-Fluoroethoxy)phenoxy]-3-[4-[3-(3-pyridyl)-2-pyridyl]piperazin-1-yl]propan-2-ol The title compound was prepared from Example 6A and 1-[3-(3-pyridyl)-2-pyridyl]piperazine following the procedure outlined for Example 1B. 1H NMR (CDCl$_3$): δ 2.33-2.37 (m, 3H, 1H D$_2$O exchanged), 2.48-2.59 (m, 4H), 2.83-2.95 (m, 4H), 3.93 (d, 2H, J=5.0 Hz), 4.01-4.07 (m, 1H), 4.17-4.28 (m, 1H), 4.50-4.65 (m, 1H), 6.54-6.58 (m, 2H), 6.85-6.87 (m, 2H), 6.96 (dd, 1H, J=7.4 Hz), 7.33-7.37 (m, 1H), 7.45-7.48 (m, 1H), 7.97 (dt, 1H, J=1.9, 7.7 Hz), 8.28 (dd, 1H, J=1.9, 4.9 Hz), 8.56 (dd, 1H, J=1.7, 4.9 Hz), 8.82 (d, 1H, J=1.7 Hz). GC-MS m/z 453 (M$^+$1, 1), 452 (M$^+$, 5), 432 (36), 254 (100), 198 (29), 184 (63), 172 (45).

Example 8

1-[4-(2-Fluoroethoxy)phenoxy]-3-[4-[3-(4-pyridyl)-2-pyridyl]piperazin-1-yl]propan-2-ol The title compound was prepared from Example 6A and 1-[3-(4-pyridyl)-2-pyridyl]piperazine following the procedure outlined for Example 1B. $^1$H NMR (CDCl$_3$): δ 2.34-2.42 (m, 3H, 1H D$_2$O exchanged), 2.49-2.70 (m, 4H), 3.14 (br s, 4H), 3.92 (d, 2H, J=4.7 Hz), 4.02-4.07 (m, 1H), 4.18-4.30 (m, 1H), 4.51-4.66 (m, 1H), 6.54-6.58 (m, 2H), 6.85-6.88 (m, 2H), 6.96 (dd, 1H, J=7.4 Hz), 7.48 (dd, 1H, J=1.9, 7.4 Hz), 7.58 (d, 2H, J=4.7 Hz), 8.29 (dd, 1H, J=1.9, 4.9 Hz), 8.66 (d, 2H, J=4.9 Hz). GC-MS m/z 53 (M$^+$1, 1), 452 (M$^+$, 3), 432 (19), 253 (85), 198 (70), 184 (100).

Example 9

1-[4-[2-(4-Methoxyphenyl)phenyl]piperazin-1-yl]-3-pyrimidin-2-yloxy-propan-2-ol

9A) 2-(Oxiran-2-ylmethoxy)pyrimidine

A solution of 2 (1H)-pyrimidinone (0.61 g, 4 mmol) and glycidol (0.30 g, 4 mmol) in DMF (10 mL) was added dropwise to a stirred suspension of NaH (0.14 g, 6 mmol) in DMF (5 mL). The reaction mixture is stirred at r. t. until the reagents disappeared (TLC). The reaction mixture is taken up with brine and extracted with EtOAc (3×20 mL). The organic phases are separated, dried over Na$_2$SO$_4$ and evaporated under reduced pressure. The crude residue was chromatographed (Petroleum ether/AcOEt, 1:1, as eluent) to afford pure compound in 30% yield. $^1$H NMR (CDCl$_3$): δ 2.60-2.70 (m, 2H), 3.16 (m, 1H), 3.89-4.04 (m, 2H), 4.17-4.28 (m, 1H), 4.50-4.65 (m, 1H), 7.00 (t, 1H, J=7.4 Hz), 8.56 (d, 2H, J=4.9 Hz).

9B) 1-[4-[2-(4-Methoxyphenyl)phenyl]piperazin-1-yl]-3-pyrimidin-2-yloxy-propan-2-ol The title compound was prepared from Example 9A and 1-[2-(4-methoxyphenyl)phenyl]piperazine following the procedure outlined for Example 1B. $^1$H E NMR (CDCl$_3$): δ 2.34-2.42 (m, 3H, 1H D$_2$O exchanged), 2.49-2.70 (m, 4H), 3.14 (br s, 4H), 3.80 (s, 3H), 3.92 (d, 2H, J=4.7 Hz), 4.02-4.07 (m, 1H), 6.33 (dd, 1H, J=1.9, 7.4 Hz), 6.60-6.65 (m, 3H), 6.77-6.65 (m, 3H), 7.00 (t, 1H, J=7.4 Hz), 7.09-7.13 (m, 1H), 8.56 (d, 2H, J=4.9 Hz).

Example 10

1-[4-[2-(4-Methoxyphenyl)phenyl]piperazin-1-yl]-3-pyrazin-2-yloxy-propan-2-ol

10A) 2-(Oxiran-2-ylmethoxy)pyrazine

Title compound was prepared starting from 3-(2H)pyridazone following the same procedure outlined for Example 9A. $^1$H R NMR (CDCl$_3$): δ 2.60-2.70 (m, 2H), 3.16 (m, 1H), 3.89-4.04 (m, 2H), 4.17-4.28 (m, 1H), 4.50-4.65 (m, 1H), 8.13 (d, 1H, 7.2 Hz), 8.15-8.20 (m, 1H), 8.23 (dd, 1H, J=1.9, 4.9 Hz).

10B) 6. 1-[4-[2-(4-Methoxyphenyl)phenyl]piperazin-1-yl]-3-pyrazin-2-yloxy-propan-2-ol The title compound was prepared from Example 10A and 1-[2-(4-methoxyphenyl)phenyl]piperazine following the procedure outlined for Example 1B. $^1$H NMR (CDCl$_3$): δ 2.34-2.42 (m, 3H, 1H D$_2$O exchanged), 2.49-2.70 (m, 4H), 3.14 (br s, 4H), 3.80 (s, 3H), 3.92 (d, 2H, J=4.7 Hz), 4.02-4.07 (m, 1H), 6.33 (dd, 1H, J=1.9, 7.4 Hz), 6.60-6.65 (m, 3H), 6.77-6.65 (m, 3H), 7.09-7.13 (m, 1H), 8.13 (d, 1H, J=7.4 Hz), 8.16-8.19 (m, 1H), 8.23 (d, 1H, J=1.9, 7.4 Hz).

Example 11

1-[4-[2-(4-Methoxyphenyl)phenyl]piperazin-1-yl]-3-pyrimidin-4-yloxy-propan-2-ol 11A) 4-(Oxiran-2-ylmethoxy)pyrimidine Title compound was prepared starting from 4(3H)-pyrimidinone following the same procedure outlined for Example 9A. $^1$H NMR (CDCl$_3$): δ 2.60-2.70 (m, 2H), 3.16 (m, 1H), 3.89-4.04 (m, 2H), 4.17-4.28 (m, 1H), 4.50-4.65 (m, 1H), 6.29 (dd, 1H, J=1.9, 7.4 Hz), 8.44 (dd, 1H, J=1.9, 7.4 Hz), 8.70-8.73 (m, 1H).

11B) 1-[4-[2-(4-Methoxyphenyl)phenyl]piperazin-1-yl]-3-pyrimidin-4-yloxy-propan-2-ol The title compound was prepared from Example 11A and 1-[2-(4-methoxyphenyl)phenyl]piperazine following the procedure outlined for Example 1B. $^1$H NMR (CDCl$_3$): δ 2.34-2.42 (m, 3H, 1H D$_2$O exchanged), 2.49-2.70 (m, 4H), 3.14 (br s, 4H), 3.80 (s, 3H), 3.92 (d, 2H, J=4.7 Hz), 4.02-4.07 (m, 1H), 6.33 (dd, 1H, J=1.9, 7.4 Hz), 6.60-6.65 (m, 3H), 6.77-6.65 (m, 3H), 7.09-7.13 (m, 1H), 8.13 (d, 1H, J=7.4 Hz), 8.16-8.19 (m, 1H), 8.23 (d, 1H, J=1.9, 7.4 Hz).

Example 12

1-[2-Fluoro-2-(3-methoxyphenyl)ethyl]-4-[3-(2-pyridyl)-2-pyridyl]piperazine 12A) 1-(3-Methoxyphenyl)-2-[4-[3-(2-pyridyl)-2-pyridyl]piperazin-1-yl]ethanone A stirred mixture of 2-bromo-1-(3-methoxyphenyl)ethanone (0.5 g, 2.2 mmol), 1-[3-(2-pyridyl)-2-pyridyl]piperazine (0.6 g, 2.6 mmol) and K$_2$CO$_3$ (3 mmol) in acetonitrile was refluxed overnight. After cooling, the mixture was evaporated to dryness and H$_2$O (20 mL) was added to the residue. The aqueous phase was extracted with AcOEt (2×30 mL). The collected organic layers were dried over Na$_2$SO$_4$ and evaporated under reduced pressure. The crude residue was chromatographed (CHCl$_3$/AcOEt, 9:1, as eluent) to afford pure compound in quantitative yield. $^1$H NMR (CDCl$_3$): δ 2.52 (br s, 4H), 2.93 (app t, 4H), 3.78 (s, 2H), 3.80 (s, 3H), 6.84-6.90 (m, 3H), 7.04-7.10 (m, 2H) 7.20-7.26 (m, 1H), 7.71 (dd, 1H, J=1.6, 7.4 Hz), 7.83 (dt, 1H, J=1.9, 7.4 Hz), 7.88-7.92 (m, 1H), 8.27 (dd, 1H, J=1.9, 4.9 Hz), 8.69-8.72 (m, 1H). GC-MS m/z 387 (M$^+$1, 2), 390 (M$^+$, 8), 254 (100), 184 (63).

12 B ) 1-(3-Methoxyphenyl)-2-[4-[3-(2-pyridyl)-2-pyridyl]piperazin-1-yl]ethanol.

To a solution of 7A (0.3 g, 0.7 mmol) in MeOH (15 mL) NaBH$_4$ (40 mg, 1.01 mmol) was added and the mixture was stirred at r.t for 3-4 h. Then the reaction mixture was quenched with H$_2$O. MeOH was removed under reduced pressure and the aqueous solution was extracted with CH$_2$Cl$_2$ (3×20 mL). The organic phases were collected, washed with brine, dried over Na$_2$SO$_4$ and concentrated in vacuo. The crude residue was purified by chromatography (CHCl$_3$/AcOEt, 9:1 as eluent) to give pure compound as oil (40% yield). $^1$H NMR (CDCl$_3$): δ 2.42-2.48 (m, 4H), 2.62-2.66 (m, 3H, 1H D$_2$O exchanged), 2.91-3.01 (m, 4H), 3.80 (s, 3H), 4.78-4.82 (m, 1H), 6.84-6.90 (m, 3H), 7.04-7.10 (m, 2H) 7.20-7.26 (m, 1H), 7.71 (dd, 1H, J=1.6, 7.4 Hz), 7.83 (dt, 1H, J=1.9, 7.4 Hz), 7.88-7.92 (m, 1H), 8.27 (dd, 1H, J=1.9, 4.9 Hz), 8.69-8.72 (m, 1H). GC-MS m/z 391 (M$^+$1, 1), 390 (M$^+$, 1), 372 (10), 254 (100), 184 (63).

12C) 1-[2-Fluoro-2-(3-methoxyphenyl)ethyl]-4-[3-(2-pyridyl)-2-pyridyl]piperazine A solution of 7B (0.25 g, 0.6 mmol) in 10 mL CH$_2$Cl$_2$ was cooled at 0° C. and a solution 50% p/v of deoxofluor in THF was added (0.3 mL, 0.63 mmol). The mixture was stirred at r.t. for 2 h. Then, the mixture was washed with a saturated aqueous solution of NaHCO$_3$ (20 mL) and with H$_2$O (20 mL). The organic phases were collected, dried over Na$_2$SO$_4$ and concentrated in vacuo. The crude residue was purified by chromatography (CHCl$_3$/AcOEt, 9:1 as eluent) to give pure compound as oil (45% yield). $^1$H NMR (CDCl$_3$): δ 2.50-2.60 (m, 4H), 2.66-2.93 (m, 2H), 3.14 (app t, 4H), 3.81 (s, 3H), 5.30-5.71 (m, 1H), 6.84-6.90 (m, 3H), 7.04-7.10 (m, 2H) 7.20-7.26 (m, 1H), 7.71 (dd, 1H, J=1.6, 7.4 Hz), 7.83 (dt, 1H, J=1.9, 7.4 Hz), 7.88-7.92 (m, 1H), 8.27 (dd, 1H, J=1.9, 4.9 Hz), 8.69-8.72 (m, 1H). GC-MS m/z 393 (M$^+$1, 3), 392 (M$^+$, 3), 372 (25), 254 (100), 198 (25), 184 (63).

Example 13

1-[2-Fluoro-2-(3-methoxyphenyl)ethyl]-4-[3-(3-pyridyl)-2-pyridyl]piperazine

The title compound was prepared starting from 2-bromo-1-(3-methoxyphenyl)ethanone and 1-[3-(3-pyridyl)-2-pyridyl]piperazine following the procedure outlined for Example 12. $^1$H NMR (CDCl$_3$): δ 2.50-2.60 (m, 4H), 2.66-2.93 (m, 2H), 3.14 (app t, 4H), 3.81 (s, 3H), 5.30-5.71 (m, 1H), 6.84-6.90 (m, 3H), 7.04-7.10 (m, 2H) 7.33-7.37 (m, 1H), 7.46 (dd, 1H, J=1.9, 7.4 Hz), 7.97 (dt, 1H, J=1.9, 7.7 Hz), 8.28 (dd, 1H, J=1.9, 4.9 Hz), 8.56 (dd, 1H, J=1.7, 4.9 Hz), 8.82 (d, 1H, J=1.7 Hz). GC-MS m/z 393 (M$^+$1, 3), 392 (M$^+$, 3), 372 (30), 254 (100), 198 (29), 184 (63).

Example 14

1-[2-Fluoro-2-(3-methoxyphenyl)ethyl]-4-[3-(4-pyridyl)-2-pyridyl]piperazine

The title compound was prepared starting from 2-bromo-1-(3-methoxyphenyl)ethanone and 1-[3-(4-pyridyl)-2-pyridyl]piperazine following the procedure outlined for Example 12. 1R NMR (CDCl$_3$): δ 2.51-2.63 (m, 4H), 2.67-2.89 (m, 2H), 3.15 (br s, 4H), 3.82 (s, 3H), 5.30-5.70 (m, 1H), 6.84-6.91 (m, 3H), 7.25-7.31 (m, 2H), 7.55 (dd, 1H, J=1.9, 7.4 Hz), 7.58 (dd, 2H, J=1.7, 4.7 Hz), 8.29 (dd, 1H, J=1.9, 4.9 Hz), 8.66 (dd, 2H, J=1.7, 4.9 Hz). GC-MS m/z 4393 (M$^+$1, 1), 392 (M$^+$, 3), 372 (35), 253 (85), 198 (70), 184 (100), 172 (45).

Example 15

1-[2-(3-Methoxyphenoxy)ethyl]4-[3-(2-pyridyl)-2-pyridyl]piperazine

A stirred mixture of 1-(2-chloroethoxy)-3-methoxybenzene (0.65 g, 3.5 mmol), 1-[3-(2-pyridyl)-2-pyridyl]piperazine (0.7 g, 2.9 mmol) and K$_2$CO$_3$ (3.5 mmol) in DMF was refluxed overnight. After cooling, the mixture was evaporated to dryness and H$_2$O (20 mL) was added to the residue. The aqueous phase was extracted with AcOEt (2×30 mL). The collected organic layers were dried over Na$_2$SO$_4$ and evaporated under reduced pressure. The crude residue was chromatographed (CHCl$_3$/AcOEt, 9:1, as eluent) to afford pure compound in 77% yield.

$^1$H NMR (CDCl$_3$): δ 2.48 (br s, 4H), 2.78 (t, 2H, J=6.0 Hz), 2.87 (app t, 4H), 3.78 (s, 3H), 4.07 (t, 2H, J=6.0 Hz), 6.45-6.52 (m, 3H), 7.05-7.12 (m, 2H) 7.20-7.26 (m, 1H), 7.71 (dd, 1H, J=1.6, 7.4 Hz), 7.83 (dt, 1H, J=1.9, 7.4 Hz), 7.88-7.92 (m, 1H), 8.27 (dd, 1H, J=1.9, 4.9 Hz), 8.69-8.72 (m, 1H). GC-MS m/z 391 (M$^+$1, 1), 390 (M$^+$, 10), 267 (40), 253 (100), 198 (26), 184 (54).

Example 16

1-[2-(3-Methoxyphenoxy) ethyl]-4-[3-(3-pyridyl)-2-pyridyl]piperazine

The title compound was prepared starting from 1-(2-chloroethoxy)-3-methoxybenzene and 1-[3-(3-pyridyl)-2-pyridyl]piperazine following the procedure outlined for Example 15. $^1$H NMR (CDCl$_3$): δ 2.48 (br s, 4H), 2.77 (t, 2H, J=6.0 Hz), 2.88 (app t, 4H), 3.78 (s, 3H), 4.06 (t, 2H, J=6.0 Hz), 6.45-6.52 (m, 3H), 7.04-7.10 (m, 2H) 7.33-7.37 (m, 1H), 7.46 (dd, 1H, J=1.9, 7.4 Hz), 7.97 (dt, 1H, J=1.9, 7.7 Hz), 8.28 (dd, 1H, J=1.9, 4.9 Hz), 8.56 (dd, 1H, J=1.7, 4.9 Hz), 8.82 (d, 1H, J=1.7 Hz). GC-MS m/z 391 (M$^+$1, 3), 390 (M$^+$, 3), 267 (35), 253 (100), 198 (29), 184 (63).

Example 17

1-[2-(3-Methoxyphenoxy)ethyl]4-[3-(4-pyridyl)-2-pyridyl]piperazine

The title compound was prepared starting from 1-(2-chloroethoxy)-3-methoxybenzene and 1-[3-(4-pyridyl)-2-pyridyl]piperazine following the procedure outlined for Example 15. $^1$H NMR (CDCl$_3$): δ 2.47-2.52 (m, 4H), 2.75 (t, 2H, J=5.9 Hz), 2.92 (br s, 4H), 3.77 (s, 3H), 4.05 (t, 2H, J=5.9 Hz), 6.47-6.54 (m, 3H), 7.01-7.09 (m, 2H), 7.56 (dd, 1H, J=1.9, 7.4 Hz), 7.60 (dd, 1H, J=1.7, 4.7 Hz), 8.29 (dd, 1H, J=1.9, 4.9 Hz), 8.66 (dd, 2H, J=1.7, 4.9 Hz). GC-MS m/z 391 (M$^+$1, 1), 390 (M$^+$, 8), 267 (35), 253 (100), 198 (10), 184 (40).

Example 18

1-[2-[4-(2-Fluoroethoxy)phenoxy]ethyl]-4-[3-(2-pyridyl)-2-pyridyl]piperazine

The title compound was prepared starting from 1-(2-chloroethoxy)-3-methoxybenzene and 1-[3-(2-pyridyl)-2-pyridyl]piperazine following the procedure outlined for Example 15. $^1$H NMR (CDCl$_3$): δ 2.48 (br s, 4H), 2.78 (t, 2H, J=6.0 Hz), 2.87 (app t, 4H), 4.07 (t, 2H, J=6.0 Hz), 4.18-4.30 (m, 2H), 4.67-4.86 (m, 2H), 6.45-6.52 (m, 2H), 7.05-7.12 (m, 2H) 7.20-7.26 (m, 3H), 7.71 (dd, 1H, J=1.6, 7.4 Hz), 7.83 (dt, 1H, J=1.9, 7.4 Hz), 7.88-7.92 (m, 1H), 8.27 (dd, 1H, J=1.9, 4.9 Hz), 8.69-8.72 (m, 1H). GC-MS m/z 423 (M$^+$1, 1), 422 (M$^+$, 4), 402 (30), 267 (25), 253 (100), 198 (26), 184 (54).

Example 19

1-[2-[4-(2-Fluoroethoxy)phenoxy]ethyl]-4-[3-(3-pyridyl)-2-pyridyl]piperazine

The title compound was prepared starting from 1-(2-chloroethoxy)-3-methoxybenzene and 1-[3-(3-pyridyl)-2-pyridyl]piperazine following the procedure outlined for Example 15. 1R NMR (CDCl$_3$): δ 2.45 (br s, 4H), 2.76 (t, 2H, J=6.0 Hz), 2.88 (app t, 4H), 4.05 (t, 2H, J=6.0 Hz), 4.14-4.28 (m, 2H), 4.69-4.85 (m, 2H), 6.48-6.53 (m, 3H), 7.04-7.10 (m, 2H) 7.33-7.37 (m, 3H), 7.45 (dd, 1H, J=1.9, 7.4 Hz), 7.95 (dt, 1H, J=1.9, 7.7 Hz), 8.29 (dd, 1H, J=1.9, 4.9 Hz), 8.55 (dd, 1H, J=1.7, 4.9 Hz), 8.80 (d, 1H, J=1.7 Hz). GC-MS m/z 423 (M$^+$1, 1), 422 (M$^+$, 5), 402 (20), 267 (40), 253 (100), 184 (63).

Example 20

1-[2-[4-(2-Fluoroethoxy)phenoxy]ethyl]-4-[3-(4-pyridyl)-2-pyridyl]piperazine

The title compound was prepared starting from 1-(2-chloroethoxy)-3-methoxybenzene and 1-[3-(4-pyridyl)-2-pyridyl]piperazine following the procedure outlined for Example 15. $^1$H NMR (CDCl$_3$): δ 2.47-2.52 (m, 4H), 2.75 (t, 2H, J=5.9 Hz), 2.92 (br s, 4H), 4.05 (t, 2H, J=5.9 Hz), 4.12-4.26 (m, 2H), 4.65-4.86 (m, 2H), 6.47-6.54 (m, 2H), 7.01-7.09 (m, 3H), 7.56 (dd, 1H, J=1.9, 7.4 Hz), 7.60 (dd, 2H, J=1.7, 4.7 Hz), 8.29 (dd, 1H, J=1.9, 4.9 Hz), 8.66 (dd, 2H, J=1.7, 4.9 Hz). GC-MS m/z 423 (M$^+$1, 1), 422 (M$^+$, 5), 402 (15), 267 (42), 253 (100), 184 (63).

Example 21

4-[2-(4-Methoxyphenyl)phenyl]-N-(2-pyridinylmethyl)-1-piperazinehexanamide

A stirred mixture of 6-bromo-N-(2-pyridylmethyl)hexanamide (0.60 g, 2.1 mmol), 1-[2-(4-methoxyphenyl)phenyl]piperazine (0.68 g, 2.5 mmol) and K$_2$CO$_3$ (3.5 mmol) in acetonitrile was refluxed overnight. After cooling, the mixture was evaporated to dryness and H$_2$O (20 mL) was added to the residue. The aqueous phase was extracted with AcOEt (2×30 mL). The collected organic layers were dried over Na$_2$SO$_4$ and evaporated under reduced pressure. The crude residue was chromatographed (CHCl$_3$/MeOH, 19:1, as eluent) to afford pure compound in 60% yield. $^1$H NMR (CDCl$_3$): δ 1.35-1.42 (m, 2H), 1.53-1.63 (m, 2H), 1.68-1.78 (m, 2H), 2.28 (t, 2H, J=7.4 Hz), 2.42 (app. t, 2H), 2.65 (br s, 4H), 3.09 (br s, 4H), 3.81 (s, 3H), 4.45 (d, 2H, J=6.1 Hz), 6.12 (br t, 1H, D$_2$O exchanged), 6.94 (d, 2H, J=8.8 Hz), 7.00 (d, 1H, J=8.0 Hz), 7.09-7.16 (m, 2H), 7.22-7.30 (m, 3H), 7.46 (d, 2H, J=8.8 Hz), 8.58 (m, 1H). GC-MS m/z 473 (M$^+$1, 1), 472 (M$^+$, 5), 379 (20), 282 (50), 226 (100), 210 (35).

Example 22

4-[2-(4-Methoxyphenyl) phenyl]-N-(3-pyridinylmethyl)-1-piperazinehexanamide

The title compound was prepared starting from 6-bromo-N-(3-pyridylmethyl)hexanamide and 1-[2-(4-methoxyphenyl)phenyl]piperazine following the procedure outlined for Example 21. $^1$H NMR (CDCl$_3$): δ 1.35-1.42 (m, 2H), 1.53-1.63 (m, 2H), 1.68-1.78 (m, 2H), 2.28 (t, 2H, J=7.4 Hz), 2.42 (app. t, 2H), 2.65 (br s, 4H), 3.09 (br s, 4H), 3.80 (s, 3H), 4.45 (d, 2H, J=6.1 Hz), 6.12 (br t, 1H, D$_2$O exchanged), 6.94 (d, 2H, J=8.8 Hz), 7.00 (d, 1H, J=8.0 Hz), 7.09-7.12 (m, 2H), 7.20-7.28 (m, 3H), 7.46 (d, 2H, J=8.8 Hz), 8.44 (m, 1H). GC-MS m/z 473 (M$^+$1, 1), 472 (M$^+$, 4), 379 (15), 282 (65), 226 (100), 210 (43), 196 (10).

Example 23

4-[2-(4-Methoxyphenyl)phenyl]-N-(4-pyridinylmethyl)-1-piperazinehexanamide

The title compound was prepared starting from 6-bromo-N-(4-pyridylmethyl)hexa namide and 1-[2-(4-methoxyphenyl)phenyl]piperazine following the procedure outlined for Example 21. $^1$H NMR (CDCl$_3$): δ 1.34-1.43 (m, 2H), 1.53-1.63 (m, 2H), 1.67-1.77 (m, 2H), 2.28 (t, 2H, J=7.4 Hz), 2.42 (app. t, 2H), 2.66 (br s, 4H), 3.10 (br s, 4H), 3.81 (s, 3H), 4.45 (d, 2H, J=6.1 Hz), 6.10 (br t, 1H, D$_2$O exchanged), 6.94 (d, 2H, J=8.8 Hz), 7.00 (d, 1H, J=8.0 Hz), 7.09-7.16 (m, 3H), 7.22-7.30 (m, 2H), 7.46 (d, 2H, J=8.8 Hz), 8.55 (dd, 2H, J=1.4, 4.4 Hz). GC-MS m/z 473 (M$^+$1, 1), 472 (M$^+$, 5), 379 (15), 282 (82), 226 (100), 210 (43).

Example 24

N-[(4-Methoxyphenyl)methyl]-6-[4-[3-(2-pyridyl)-2-pyridyl]piperazin-1-yl]hexanamide

24A)
6-Bromo-N-(4-methoxyphenylmethyl)hexanamide

A cooled solution of (4-methoxyphenyl) methanamine (0.55 g, 4.0 mmol) in CH$_2$Cl$_2$ was stirred vigorously with 2% aqueous NaOH (9.6 mL, 4.8 mmol) while 6-bromohexanoyl chloride (4.8 mmol) in CH$_2$Cl$_2$ was added dropwise. The same NaOH solution was then used to maintain pH at 9, and at costant pH the layers were separated. The organic phase was washed with 3 N HCl, with H$_2$O, and then dried over Na$_2$SO$_4$ and evaporated under reduced pressure. The crude residue was chromatographed (CHCl$_3$/AcOEt, 1:1, as eluent) to afford pure compound in 65% yield. 1R NMR (CDCl$_3$): δ 1.43-1.53 (m, 2H), 1.65-1.73 (m, 2H), 1.83-1.92 (m, 2H), 2.26 (app. t, 2H), 3.41 (t, 2H, J=6.6 Hz), 3.81 (s, 3H), 4.49 (d, 2H, J=6.05 Hz), 5.93 (br t, 1H, D$_2$O exchanged), 7.37 (d, 2H, J=8.5 Hz), 7.59-7.63 (m, 2H).

24B) N-[(4-Methoxyphenyl)methyl]-6-[4-[3-(2-pyridyl)-2-pyridyl]piperazin-1-yl]hexanamide A stirred mixture of 6-bromo-N-(4-methoxyphenylmethyl)hexanamide (0.60 g, 1.9 mmol), 1-[3-(2-pyridyl]-2-pyridyl]piperazine (0.55 g, 2.3 mmol) and K$_2$CO$_3$ (3.5 mmol) in acetonitrile was refluxed overnight. After cooling, the mixture was evaporated to dryness and H$_2$O (20 mL) was added to the residue. The aqueous phase was extracted with AcOEt (2×30 mL). The collected organic layers were dried over Na$_2$SO$_4$ and evaporated under reduced pressure. The crude residue was chromatographed (CHCl$_3$/MeOH, 19:1, as eluent) to afford pure compound in 60% yield. $^1$H NMR (CDCl$_3$): δ 1.34-1.43 (m, 2H), 1.53-1.63 (m, 2H), 1.67-1.77 (m, 2H), 2.28 (t, 2H, J=7.4 Hz), 2.42 (app. t, 2H), 2.66 (br s, 4H), 3.10 (br s, 4H), 3.81 (s, 3H), 4.45 (d, 2H, J=6.1 Hz), 6.10 (br s, 1H, D$_2$O exchanged), 6.82-6.84 (m, 2H), 6.89-6.91 (m, 2H), 7.20-7.26 (m, 3H), 7.71 (dd, 1H, J=1.6, 7.4 Hz), 7.83 (dt, 1H, J=1.9, 7.4 Hz), 7.88-7.92 (m, 1H), 8.27 (dd, 1H, J=1.9, 4.9 Hz), 8.69-8.72 (m, 1H).

Example 25

N-[(4-Methoxyphenyl)methyl]-6-[4-[3-(3-pyridyl)-2-pyridyl]piperazin-1-yl]hexanamide The title compound was prepared starting from Example 24A and 1-[3-(3-pyridyl)-2-pyridyl]piperazine following the procedure outlined for Example 24. $^1$H NMR (CDCl$_3$): δ 1.34-1.43 (m, 2H), 1.53-1.63 (m, 2H), 1.67-1.77 (m, 2H), 2.28 (t, 2H, J=7.4 Hz), 2.42 (app. t, 2H), 2.66 (br s, 4H), 3.10 (br s, 4H), 3.81 (s, 3H), 4.45 (d, 2H, J=6.1 Hz), 6.10 (br s, 1H, D$_2$O exchanged), 6.82-6.84 (m, 2H), 6.89-6.91 (m, 2H), 7.33-7.37 (m, 2H), 7.45 (dd, 1H, J=1.9, 7.4 Hz), 7.95 (dt, 1H, J=1.9, 7.7 Hz), 8.29 (dd, 1H, J=1.9, 4.9 Hz), 8.55 (dd, 1H, J=1.7, 4.9 Hz), 8.80 (d, 1H, J=1.7 Hz).

Example 26

N-[(4-Methoxyphenyl)methyl]-6-[4-[3-(4-pyridyl)-2-pyridyl]piperazin-1-yl]hexanamide The title compound was prepared starting from Example 24A and 1-[3-(4-pyridyl)-2-pyridyl]piperazine following the procedure outlined for Example 24. $^1$H NMR (CDCl$_3$): δ 1.34-1.43 (m, 2H), 1.53-1.63 (m, 2H), 1.67-1.77 (m, 2H), 2.28 (t, 2H, J=7.4 Hz), 2.42 (app. t, 2H), 2.66 (br s, 4H), 3.10 (br s, 4H), 3.81 (s, 3H), 4.45 (d, 2H, J=6.1 Hz), 6.10 (br s, 1H, D$_2$O exchanged), 6.82-6.84 (m, 2H), 6.89-6.91 (m, 2H), 7.01-7.09 (m, 1H), 7.56 (dd, 1H, J=1.9, 7.4 Hz), 7.60 (dd, 2H, J=1.7, 4.7 Hz), 8.29 (dd, 1H, J=1.9, 4.9 Hz), 8.66 (dd, 2H, J=1.7, 4.9 Hz).

Example 27

3-[2-[4-[2-(4-Methoxyphenyl)phenyl]piperazin-1-yl]ethoxy]-N-(2-pyridylmethyl)propanamide

27A)
3-(2-Chloroethoxy)-N-(2-pyridylmethyl)propanamide

A cooled solution of (2-pyridyl)methanamine (0.55 g, 5.1 mmol) in CH$_2$Cl$_2$ was stirred vigorously with 2% aqueous NaOH (12.2 mL, 6.1 mmol) while 3-(2-chloroethoxy)propanoyl chloride (6.1 mmol, prepared by refluxing 3-(2-chloroethoxy)propanoic acid with SOCl$_2$) in CH$_2$Cl$_2$ was added dropwise. The same NaOH solution was then used to maintain pH at 9, and at costant pH the layers were separated. The organic phase was washed with 3 N HCl, with H$_2$O, and then dried over Na$_2$SO$_4$ and evaporated under reduced pressure. The crude residue was chromatographed (CHCl$_3$/AcOEt, 1:1, as eluent) to afford pure compound in 65% yield. $^1$H NMR (CDCl$_3$): δ 2.38-2.41 (m, 2H), 2.60-2.63 (m, 2H), 3.54-3.60 (m, 2H), 3.66-3.69 (m, 2H), 4.45 (d, 2H, J=6.1 Hz), 6.12 (br t, 1H, D$_2$O exchanged), 7.09-7.11 (m, 2H), 8.40-8.42 (m, 2H).

27B) 3-[2-[4-[2-(4-Methoxyphenyl)phenyl]piperazin-1-yl]ethoxy]-N-(2-pyridylmethyl)propanamide Title compound was prepared starting Example 27A and 1-[2-(4-methoxyphenyl)phenyl]piperazine following the same procedure as outlined for Example 24. $^1$H NMR (CDCl$_3$): δ 2.38-2.41 (m, 2H), 2.60-2.63 (m, 2H), 2.65 (br s, 4H), 3.09 (br s, 4H), 3.54-3.60 (m, 2H), 3.66-3.69 (m, 2H), 3.81 (s, 3H), 4.45 (d, 2H, J=6.1 Hz), 6.12 (br t, 1H, D$_2$O exchanged), 6.94 (d, 2H, J=8.8 Hz), 7.00 (d, 1H, J=8.0 Hz), 7.09-7.16 (m, 2H), 7.22-7.30 (m, 3H), 7.46 (d, 2H, J=8.8 Hz), 8.58 (m, 1H).

Example 28

3-[2-[4-[2-(4-Methoxyphenyl)phenyl]piperazin-1-yl]ethoxy]-N-(3-pyridylmethyl)propanamide

28A)
3-(2-Choloroethoxy)-N-(3-pyridylmethyl)propanamide

Title compound was prepared starting from (2-pyridyl)methanamine and 3-(2-chloroethoxy)propanoyl chloride following the procedure outlined for Example 27A. ¹H NMR (CDCl₃): δ 2.38-2.41 (m, 2H), 2.60-2.63 (m, 2H), 3.54-3.60 (m, 2H), 3.66-3.69 (m, 2H), 4.45 (d, 2H, J=6.1 Hz), 6.12 (br t, 1H, D₂O exchanged), 7.09-7.11 (m, 2H), 8.40-8.42 (m, 2H).

28B) 3-[2-[4-[2-(4-Methoxyphenyl)phenyl]piperazin-1-yl]ethoxy]-N-(3-pyridylmethyl)propanamide Title compound was prepared starting Example 28A and 1-[2-(4-methoxyphenyl)phenyl]piperazine following the same procedure as outlined for Example 24. ¹H NMR (CDCl₃): δ 2.38-2.41 (m, 2H), 2.60-2.63 (m, 2H), 2.65 (br s, 4H), 3.09 (br s, 4H), 3.54-3.60 (m, 2H), 3.66-3.69 (m, 2H), 3.80 (s, 3H), 4.30 (d, 2H, J=6.1 Hz), 6.12 (br t, 1H, D₂O exchanged), 6.94 (d, 2H, J=8.8 Hz), 7.00 (d, 1H, J=8.0 Hz), 7.09-7.12 (m, 2H), 7.20-7.28 (m, 3H), 7.46 (d, 2H, J=8.8 Hz), 8.44 (m, 1H).

Example 29

3-[2-[4-[2-(4-Methoxyphenyl)phenyl]piperazin-1-yl]ethoxy]-N-(4-pyridylmethyl)propanamide 29A)
3-(2-Chloroethoxy)-N-(4-pyridylmethyl)propanamide Title compound was prepared starting from (4-pyridyl)methanamine and 3-(2-chloroethoxy)propanoyl chloride following the procedure outlined for Example 27A. ¹H NMR (CDCl₃): δ 2.38-2.41 (m, 2H), 2.60-2.63 (m, 2H), 3.54-3.60 (m, 2H), 3.66-3.69 (m, 2H), 4.45 (d, 2H, J=6.1 Hz), 6.12 (br t, 1H, D₂O exchanged), 7.09-7.11 (m, 2H), 8.40-8.42 (m, 2H).

29B) 3-[2-[4-[2-(4-Methoxyphenyl)phenyl]piperazin-1-yl]ethoxy]-N-(4-pyridylmethyl)propanamide Title compound was prepared starting Example 29A and 1-[2-(4-methoxyphenyl)phenyl]piperazine following the same procedure as outlined for Example 24. ¹H NMR (CDCl₃): δ 2.38-2.41 (m, 2H), 2.60-2.63 (m, 2H), 2.66 (br s, 4H), 3.10 (br s, 4H), 3.54-3.60 (m, 2H), 3.66-3.69 (m, 2H), 3.81 (s, 3H), 4.45 (d, 2H, J=6.1 Hz), 6.10 (br t, 1H, D₂O exchanged), 6.94 (d, 2H, J=8.8 Hz), 7.00 (d, 1H, J=8.0 Hz), 7.09-7.16 (m, 3H), 7.22-7.30 (m, 2H), 7.46 (d, 2H, J=8.8 Hz), 8.55 (dd, 2H, J=1.4, 4.4 Hz).

Example 30

N-[(4-Methoxyphenyl)methyl]-3-[2-[4-[3-(2-pyridyl)-2-pyridyl]piperazin-1-yl]ethoxy]propanamide

30A)

3-(2-Chloroethoxy)-N-[(4methoxyphenyl)methyl]propanamide

Title compound was prepared starting from 4-methoxyphenylmethanamine and 3-(2-chloroethoxy)propanoyl chloride following the procedure outlined for Example 27A. ¹H NMR (CDCl₃): δ 2.38-2.41 (m, 2H), 2.60-2.63 (m, 2H), 3.54-3.60 (m, 2H), 3.66-3.69 (m, 2H), 3.80 (s, 3H), 4.45 (d, 2H, J=6.1 Hz), 6.12 (br t, 1H, D₂O exchanged), 6.80-6.87 (m, 4H).

30B) N-[(4-Methoxyphenyl)methyl]-3-[2-[4-[3-(2-pyridyl)-2-pyridyl]piperazin-1-yl]ethoxy]propanamide Title compound was prepared starting Example 30A and 1-[3-(2-pyridyl)-2-pyridyl]piperazine following the same procedure as outlined for Example 24. ¹H NMR (CDCl₃): δ 2.38-2.41 (m, 2H), 2.60-2.63 (m, 2H), 2.65 (br s, 4H), 3.09 (br s, 4H), 3.54-3.60 (m, 2H), 3.66-3.69 (m, 2H), 3.81 (s, 3H), 4.45 (d, 2H, J=6.1 Hz), 6.12 (br t, 1H, D₂O exchanged), 6.94 (d, 2H, J=8.8 Hz), 7.00 (d, 1H, J=8.0 Hz), 7.09-7.16 (m, 2H), 7.22-7.30 (m, 3H), 7.46 (d, 2H, J=8.8 Hz), 8.58 (m, 1H).

Example 31

N-[(4-Methoxyphenyl)methyl]-3-[2-[4-[3-(3-pyridyl)-2-pyridyl]piperazin-1-yl]ethoxy]propanamide Title compound was prepared starting Example 30A and 1-[3-(3-pyridyl)-2-pyridyl]piperazine following the same procedure as outlined for Example 24. ¹H NMR (CDCl₃): δ 2.38-2.41 (m, 2H), 2.60-2.63 (m, 2H), 2.65 (br s, 4H), 3.09 (br s, 4H), 3.54-3.60 (m, 2H), 3.66-3.69 (m, 2H), 3.81 (s, 3H), 4.45 (d, 2H, J=6.1 Hz), 6.12 (br t, 1H, D₂O exchanged), 6.82-6.84 (m, 2H), 6.89-6.91 (m, 2H), 7.33-7.37 (m, 2H), 7.45 (dd, 1H, J=1.9, 7.4 Hz), 7.95 (dt, 1H, J=1.9, 7.7 Hz), 8.29 (dd, 1H, J=1.9, 4.9 Hz), 8.55 (dd, 1H, J=1.7, 4.9 Hz), 8.80 (d, 1H, J=1.7 Hz).

Example 32

N-[(4-Methoxyphenyl)methyl]-3-[2-[4-[3-(4-pyridyl)-2-pyridyl]piperazin-1-yl]ethoxy]propanamide Title compound was prepared starting Example 30A and 1-[3-(2-pyridyl)-2-pyridyl]piperazine following the same procedure as outlined for Example 24. ¹H NMR (CDCl₃): δ 2.38-2.41 (m, 2H), 2.60-2.63 (m, 2H), 2.65 (br s, 4H), 3.09 (br s, 4H), 3.54-3.60 (m, 2H), 3.66-3.69 (m, 2H), 3.81 (s, 3H), 4.45 (d, 2H, J=6.1 Hz), 6.12 (br t, 1H, D₂O exchanged), 6.82-6.84 (m, 2H), 6.89-6.91 (m, 2H), 7.01-7.09 (m, 1H), 7.56 (dd, 1H, J=1.9, 7.4 Hz), 7.60 (dd, 2H, J=1.7, 4.7 Hz), 8.29 (dd, 1H, J=1.9, 4.9 Hz), 8.66 (dd, 2H, J=1.7, 4.9 Hz).

Analysis of the Compounds

All the compounds were analyzed by means of a Varian Mercury-VX spectrometer (for NMR spectra), HP6890-5973 MSD gas chromatograph/mass spectrometer or Agilent 1100 Series LC-MSD trap System VL workstation (for mass spectra) The purity of the compounds were determined by HPLC on a Perkin-Elmer series 200 LC instrument using a Phenomenex Prodigy ODS-3 RP-18 column, (250×4.6 mm, 5 μm particle size) and equipped with a Perkin-Elmer 785A UV/VIS detector setting 0.254 nm.

The enantiomeric purity of the compounds were determined by HPLC using a Diacell ChiralCell OD (250×4.6 mm, 10 μm particle size)

Biological Testing

Radioligand Binding Assay At Human Cloned 5-HT7 Receptors

Functionality assays on the 5-HT7 receptor were done according to Jasper et al [Br. J. Pharmacol. 1997, 122, 126.] with minor modifications. The test is a competition assay based on binding of [³H]-5-CT at human cloned 5-HT7 receptor. In 0.5 mL of incubation buffer (50 mM Tris-HCl, 10 mM MgSO₄ and 0.5 mM EDTA, pH 7.4) were suspended 34 μg of membranes, 1.5 nM [³H]-5-CT, the drugs or reference compound (six to nine concentrations). The samples were incubated for 120 min at 27° C. The incubation was stopped by rapid filtration on Whatman GF/C glass microfiber filters (pre-soaked in 0.3% polyethylenimine for 30 min). The filters were washed with 3×1 mL of ice-cold buffer (50 mM Tris-HCl, pH 7.4). Nonspecific binding was determined in the presence of 10 μM 5-CT. Approximately 90% of specific binding was determined under these conditions.

Radioligand Binding Assay At Human Cloned 5-HT$_{1A}$ Receptor

Human 5-HT$_{1A}$ serotonin receptors stably expressed in HEK293-EBNA cells were radiolabeled with 1.0 nM [$^3$H]-8-OH-DPAT [J. Biol. Chem. 1989, 264, 14848]. Samples containing 32 μg of membrane protein, different concentrations of each compound ranging from 0.1 nM to 10 μM were incubated in a final volume of 500 μL of 50 mM Tris-HCl pH 7.4, 5 mM MgSO$_4$ for 120 min at ° C. After this incubation time, samples were filtered through Whatman GF/C glass microfiber filters pre-soaked in polyethylenimine 0.5% for at least 30 min prior to use. The filters were washed twice with 1 ml of ice-cold buffer (50 mM Tris-HCl, pH 7.4). Nonspecific binding was determined in the presence of 10 μM 5-HT.

Competition binding data were analyzed using the Graph-Pad Prism Software (GraphPad Software, Inc., San Diego, Calif., USA). The value for the inhibition constant, K$_i$, was calculated by using the Cheng-Prusoff equation [Anal. Biochem. 1980, 107, 200-239].

Determination of in vitro Metabolic Stability Using Liver S9 Fractions

Tested compounds (10 μM) were incubated with rat liver S9 fractions (1 mg/ml), liver S9 fractions are subcellular fractions that contain drug-metabolizing enzymes such as cytochromes P450, flavin monooxygenases, and UDP glucuronyl transferases.

The incubation was performed in 100 mM phosphate buffer (pH 7.4) containing 1.3 mM of NADP+, 3.3 mM glucose 6-phosphate and 0.4 U/ml glucose 6-phosphate dehydrogenase, 3.3 mM MgCl2 in a total volume of 1 mL. Incubations were commenced with the addition of glucose 6-phosphate dehygrogenase and carried out for 30 min. at 37° C. The reaction was stopped by adding 1 mL of cooled acetonitrile. The samples were centrifuged at 4600 rpm for 10 min at 4° C. The supernatant was separated and the acetonitrile phase was analyzed by using a reversed-phase HPLC equipped with a Perkin-Elmer series 200 LC pump and a Perkin-Elmer 785A UV/VIS detector. UV signals were monitored and obtained peaks integrated using a personal computer running Perkin-Elmer Turbochrom Software. The column used was a Phenomenex Gemini C-18 (250×4.6 mm, 5 μm particle size). The samples were eluted with ammonium formate (20 mM; pH 6.7) and acetonitrile 80:20 v/v at a flow rate of 1 mL/min and at the appropriate UV wavelength. The sample injection volume was 20 μL.

This assay provides information on the xenobiotic metabolism of the tested compounds; the results obtained are reported in table 1.

Evaluation of Inhibition Activity of the Compounds

The compounds were active at 5-HT7 receptors because they showed Ki values lower than 100 nM in the radioligand binding assay.

Biological data on several compounds of the present invention are reported in Table 1.

TABLE 1

| | compound | | |
|---|---|---|---|
| | 5-HT$_7$ (pKi) nM | 5-HT$_{1A}$ (% displacement of radioligand at 10−7M conc.) | % parent compound after incubation with rat liver S9 fractions |
| Example 1 | 7.78 | 46 | 35 |
| Example 5 | 8.12 | 26 | 82 |
| Example 12 | 8.16 | 25 | 84 |
| Example 15 | 8.27 | 35 | 78 |
| Example 18 | 7.70 | 20 | 68 |
| Example 21 | 8.79 | 37 | 55 |
| Example 24 | 8.24 | 31 | 80 |

REFERENCES

1) Hoyer, D. et al. Pharmacol. Biochem. Behav. 2002, 71, 533.
2) Hedlund, P. B. & Sutcliffe, J. G. Trends Pharmacol. Sci. 2004, 25, 481.
3) Hedlund, P. B. Psychopharmacology (Berl). 2009, 206, 345.
Mnie-Filali, O. et al. Curr Drug Targets. 2009, 10, 1109.
4) Abbas, A. I. et al. Psychopharmacology (Berl) 2009, 205, 119.
5) Lawler, C. P. et al. Neuropsychopharmacology 1999, 20, 612.
6) Shapiro, D. A. et al. Neuropsychopharmacology 2003, 28, 1400.
7) Berman, R. M. et al. CNS Spectr. 2009, 14, 197.
8) Brenchat, A. et al. Pain 2009, 141, 239.
9) Perez-García, G. S. & Meneses, A. Behav. Brain Res. 2005, 163, 136.
10) Leo, D. et al. Genes Brain Behav. 2009, 3, 356.
11) Kvachnina, E. et al. ; J. Neurosci. 2005, 25, 7821
12) Monti JM et al. Behav Brain Res. 2008 Aug. 22; 191 (2)

The invention claimed is:
1. A compound having the following formula IV:

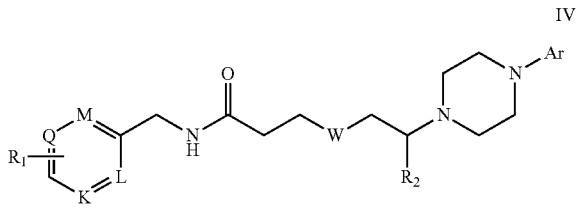

wherein W is O;
K, L, M and Q is CH or nitrogen;
R$_1$ is hydrogen;
R$_2$ is hydrogen; and
Ar is an aromatic ring with the following formula:

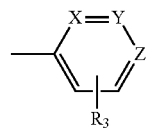

wherein X, Y and Z is CH; and R$_3$ is a five- or six-membered ring selected from the group consisting of:

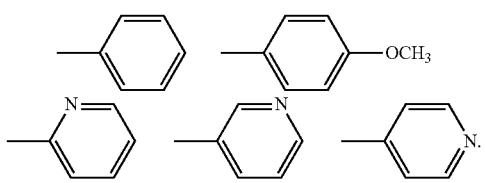

2. A compound selected from the group consisting of:
3-[2-[4-[2-(4-Methoxyphenyl)phenyl]piperazin-1-yl]ethoxy]-N-(2-pyridylmethyl)propanamide,
3-[2-[4-[2-(4-Methoxyphenyl)phenyl]piperazin-1-yl]ethoxy]-N-(3-pyridylmethyl)propanamide, and
3-[2-[4-[2-(4-Methoxyphenyl)phenyl]piperazin-1-yl]ethoxy]-N-(4-pyridylmethyl)propanamide.

3. A pharmaceutical composition comprising as active principle a compound according to claim 1 and a pharmacologically acceptable excipient and/or carrier.

4. A method for preparing a compound according to claim 1 according to the following scheme (Scheme III) comprising:

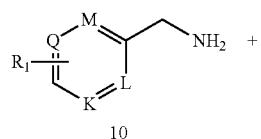

10

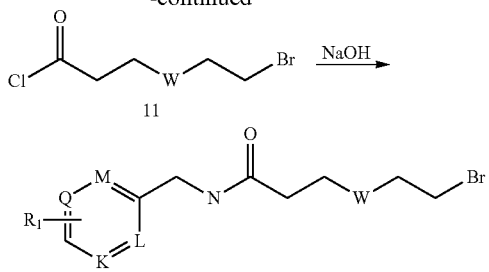

wherein all variables are as defined in claim 1, and compound 13 is isolated and optionally purified.

5. A pharmaceutical composition comprising as active principle a compound according to claim 2 and a pharmacologically acceptable excipient and/or carrier.

* * * * *